United States Patent [19]

Wan

[11] 4,234,719
[45] Nov. 18, 1980

[54] PREPARATION OF CELLULOSE ACETATE

[75] Inventor: Chee-Gen Wan, North Brunswick, N.J.

[73] Assignee: Halcon Research and Development Corp., New York, N.Y.

[21] Appl. No.: 53,612

[22] Filed: Jun. 29, 1979

Related U.S. Application Data

[63] Continuation-in-part of Ser. No. 866,089, Dec. 30, 1977.

[51] Int. Cl.³ ..................... C07B 53/08; C07C 51/15; C07C 51/54; C08B 3/06
[52] U.S. Cl. ..................................... 536/69; 260/546; 260/549; 536/71; 562/550; 562/607
[58] Field of Search ..................... 536/69, 71; 260/549, 260/546; 562/550, 607

[56] References Cited

U.S. PATENT DOCUMENTS

| 2,136,030 | 11/1938 | Stone | 536/69 |
| 2,353,255 | 7/1944 | Malm et al. | 536/69 |
| 2,521,916 | 9/1950 | Hincke et al. | 536/69 |
| 2,632,007 | 3/1953 | Blume et al. | 536/69 |
| 2,635,097 | 4/1953 | Stoneman | 536/69 |
| 2,772,944 | 12/1956 | Allewelt | 536/71 |
| 2,801,237 | 7/1957 | Clevy et al. | 536/69 |
| 2,861,069 | 11/1958 | Touey et al. | 536/69 |
| 4,002,677 | 1/1977 | Naglieri et al. | 260/546 |
| 4,002,678 | 1/1977 | Naglieri et al. | 260/549 |
| 4,046,807 | 9/1977 | Kuckertz | 260/549 |
| 4,115,444 | 9/1978 | Rizkalla | 260/549 |

Primary Examiner—Ronald W. Griffin
Attorney, Agent, or Firm—William C. Long; David Dick; Riggs T. Stewart

[57] ABSTRACT

Cellulose acetate is produced from methanol, carbon monoxide and cellulose in an integrated series of steps wherein acetic anhydride produced in a first step by the carbonylation of methyl acetate is used to acetylate cellulose to produce cellulose acetate and to co-produce acetic acid, the co-produced acetic acid is dehydrated and the dehydrated acetic acid reacted with methanol to produce methyl acetate which is then fed to the first step and carbonylated to produce additional quantities of acetic anhydride.

5 Claims, 1 Drawing Figure

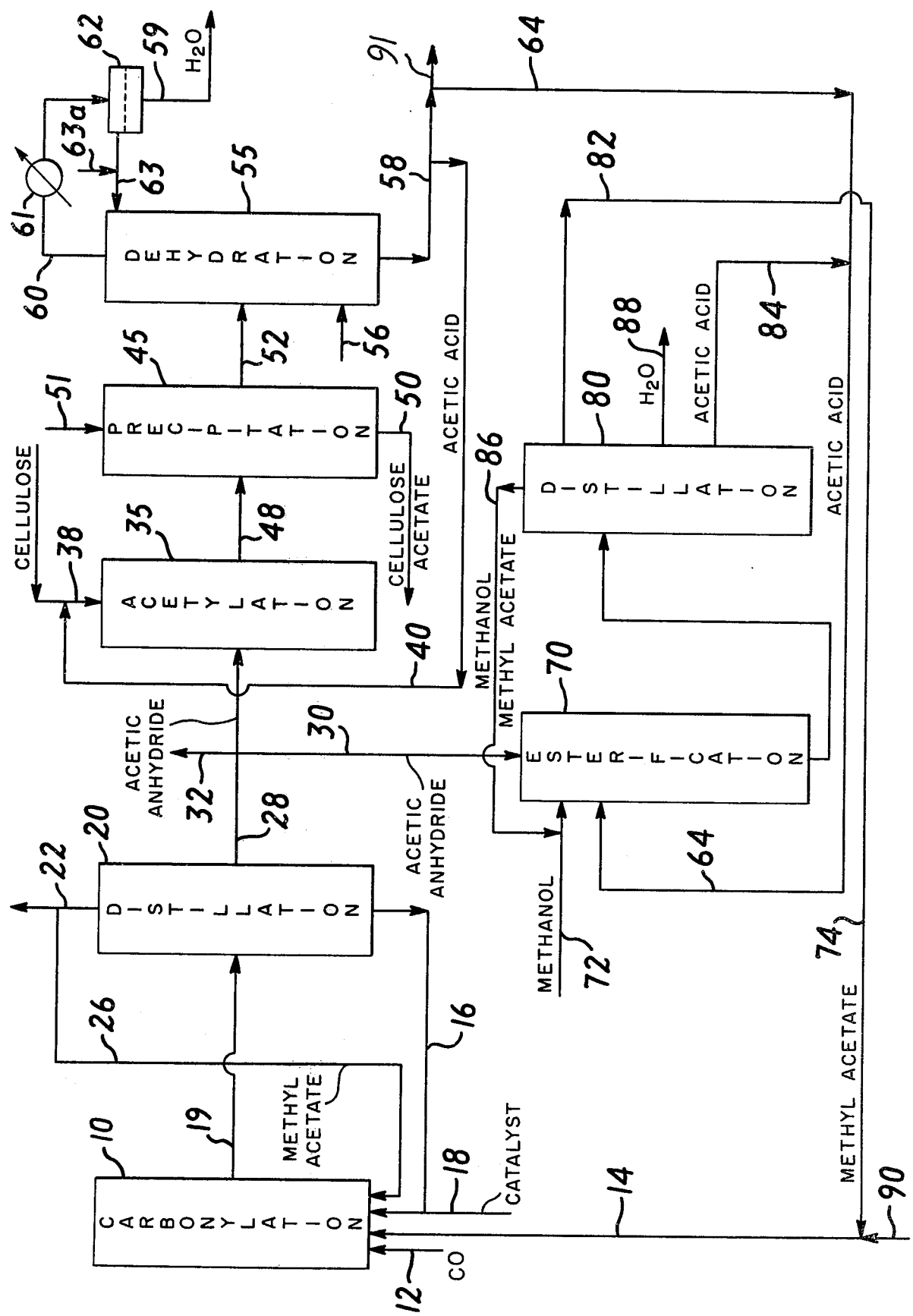

PREPARATION OF CELLULOSE ACETATE

REFERENCE TO RELATED APPLICATION

This is a continuation-in-part of co-pending application Ser. No. 866,089, filed Dec. 30, 1977.

This invention relates to the preparation of cellulose acetate and is more particularly concerned with a process for producing cellulose acetate in an integrated series of steps which permit the production of this ester from methanol, carbon monoxide and cellulose.

Cellulose acetate is a well-known industrial product which has been produced for many years in large quantities. It has commonly been produced on an industrial scale by the reaction of acetic anhydride upon cellulose in various forms, e.g., cotton linters, wood pulp and corresponding forms of raw cellulose, or fibers formed from regenerated cellulose, or textiles formed from such fibers, or the like. In each case, the cellulose molecules are acetylated to the desired degree by means of acetic anhydride, the acetic anhydride being produced by supplying acetic acid which is converted to ketene and the ketene then converted to the desired anhydride by treatment with additional acetic acid.

It is an object of this invention to provide a novel process for producing cellulose acetate wherein the raw materials, other than cellulose, are methanol and carbon monoxide.

In accordance with the invention, acetic anhydride is produced by the carbonylation of methyl acetate in an anhydrous system, the so-produced acetic anhydride is reacted with a cellulose substrate to produce cellulose acetate and to co-produce acetic acid, and the co-produced acetic acid is converted to methyl acetate which is supplied to the carbonylation step wherein acetic anhydride is produced, and the cycle is repeated.

More specifically, the co-produced acetic acid is reacted directly with methanol in an esterification reaction and the thus-produced methyl acetate is reacted with carbon monoxide to form acetic anhydride. Thus, the cellulose acetate is produced solely from methanol, carbon monoxide and cellulose and there is no need for a feed of acetic acid to the system. There is, therefore, made possible the production of cellulose acetate from methanol, carbon monoxide and cellulose in a fully integrated system, the methanol and carbon monoxide alone being the source of the acetate moiety in the product cellulose acetate.

The invention will be more readily understood by reference to the accompanying drawing which shows, diagrammatically, and solely for purposes of facile exemplification, a typical reaction system for carrying out the process of the invention. Thus, referring to the drawing, the reference numeral 10 designates a carbonyation zone, which may comprise one or more pressure reactors of any convenient type, which is fed with carbon monoxide and methyl acetate along with recycle streams and which contains a suitable catalyst, typically one comprising a metal of Group VIII of the Periodic Table, in combination with iodine or bromine moieties, generally in a liquid-phase reaction system. Thus, carbon monoxide, in pure or diluted form, is supplied via line 12 and the methyl acetate enters via line 14. The catalyst, if removed with the reaction effluent, is recycled, as will be described below, via line 16, and make-up catalyst components are supplied, as needed, via line 18. The carbonylation can be effected batch-wise, if desired, but it will be apparent that it can be readily carried out continuously and, for commercial purposes, continuous operation is preferred. The same is true for the subsequent steps of the process of the invention which will be described below. Carbonylation is typically carried out at temperatures of 20° C. to 500° C., preferably 100° to 300° C., under a carbon monoxide partial pressure of 0.1 to 15,000 psi.

From zone 10, the reaction mixture is withdrawn via line 19 and is separated into its principal components. For this purpose the mixture is passed to a distillation zone 20 which is defined by one or more distillation units, e.g., flash and/or fractional distillation devices, as will be apparent to persons skilled in the art. If the carbonylation zone is operated in typical manner entirely in the liquid phase, the entire reaction mixture, including the Group VIII catalyst, is removed for separation. On the other hand, if carbonylation is carried out as a boiling reaction, the effluent will be in the vapor phase and the relatively non-volatile catalyst will remain in the boiling liquid body in the carbonylation zone. The low-boiling components of the mixture, including methyl acetate, methyl iodide, and the like are removed through line 22, and suitably at least partially recycled via line 26 to carbonylation zone 10. The high boiling components of the reaction mixture, including the essentially non-volatile catalyst components, if present, are recycled to carbonylation zone 10 via previously-mentioned line 16 which communicates with line 18. The product acetic anhydride is withdrawn through line 28. A portion of the acetic anhydride thus separated can be diverted through line 30 to be used in the esterification reaction to be described below to produce methyl acetate to be used as feed to the carbonylation reaction. If it is desired to withdraw acetic anhydride as a co-product, this can be effected through line 32.

The bulk of the acetic anhydride in line 28 proceeds to the next step of the process for the eventual production of the desired cellulose acetate. In this step, the acetic anhydride is brought into contact in zone 35 with cellulose supplied to zone 35 through line 38, in the presence of acetic acid fed via line 40. Suitably, the cellulose to be treated is first activated by pre-soaking in acetic acid from line 40, e.g. for 10 minutes to 10 hours at 20° to 50° C., typically for about 1-2 hours at about room temperature, in accordance with conventional practice, the amount of acid being 0.25-10 parts by weight per part of cellulose, typically about 1-8 parts per part, preferably in the presence of a small amount of the catalyst to be used in the cellulose acetate forming reaction, e.g. sulfuric acid, benzene sulfonic acid, an acid-reacting ion exchange resin, and the like, although the use of the catalyst is not necessary. The activated or pre-soaked cellulose then passes via line 38 to acetylation zone 35.

In zone 35 the acetic anhydride produced as above described and the cellulose are brought together in the presence of an acetylation catalyst of the character specified above in order to effect acetylation of the cellulose by means of the acetic anhydride in conventional manner.

In the acetylation zone, the cellulose is acetylated by the acetic anhydride in the presence of the catalyst and in the presence of a solvent. In accordance with this invention, the solvent is most suitably acetic acid which is fed to the acetylation zone via line 40. The acetic acid can be mixed with the acetic anhydride prior to introduction into zone 35 or the acid and the anhydride can be added separately, the catalyst preferably being fed with the acetic acid. The ratio of acetic anhydride and solvent, e.g. acetic acid, can vary, as is well-known to persons skilled in the art, but typically the acetic anhydride is at least half of the quantity of acetic acid, including the acetic acid used in the pre-treatment, and can range up to about 10 parts by weight per part of acetic acid. Indeed, when large amounts of acetic acid have been used in the pre-treatment, only acetic anhydride and catalyst are added to the pre-treated cellulose and additional acetic acid solvent is not required. The amount of acetic anhydride is that which is conventionally used in this art and generally is in the range of 3 to 4 parts per part of cellulose. When the acetylation is carried out batch-wise, e.g. in a mixer of the Werner-Pfleiderer type, which has cooled mixing blades and cooled walls, the reaction liquid comprising the acetic anhydride, acetic acid and catalyst is preferably supplied step-wise in order to avoid excess heat generation and the liquid and the cellulose are thoroughly mixed until the desired degree of acetylation is achieved. The amount of catalyst can vary as is well-known to persons skilled in the art but is typically 1 to 5 percent by weight of the cellulose.

The degree of acetylation is then adjusted as desired in conventional manner by hydrolysis if less than fully acetylated cellulose acetate is desired, and the cellulose acetate is precipitated by means of dilute aqueous acetic acid in known manner in a zone or zones diagrammatically represented in the drawing as precipitation zone 45. The precipitated cellulose is separated from the aqueous acetic acid and withdrawn via line 50 for eventual washing and drying in accordance with known techniques. Precipitation dilutes the acetic acid contained in the reaction mixture and it is further diluted when the precipitated cellulose recovered from the reaction mixture is washed with water to remove reaction liquid. The treatment of the recovered cellulose is effected in conventional manner well-known to persons skilled in the art and such treatment is not involved in the process of this invention. Part of the dilute acetic acid thus recovered is recycled to the precipitation step to precipitate additional quantities of cellulose acetate and the remainder of the dilute acetic acid is then concentrated or dehydrated by distillation, most suitably azeotropic distillation in conventional manner.

Thus, the liquid effluent from precipitation zone 45, primarily comprising dilute aqueous acetic acid, some of which is suitably returned to zone 45 to precipitate further quantities of cellulose acetate, as mentioned, is passed via line 52 to dehydration zone 55 in which the acetic acid is dehydrated, e.g. by azeotropic distillation, to produce glacial acetic acid. In zone 55, which may consist of one or more distillation columns, the dilute aqueous acetic acid from precipitation zone 45, supplemented by dilute acid from the washing of the cellulose acetate withdrawn via line 50, the last-named dilute acid entering through line 56, is recovered in substantially anhydrous form for use in preparing methyl acetate and for recycling to the acetylation reaction. The dehydrated acetic acid is withdrawn through line 58 and the removed water is withdrawn via line 59. Most suitably the dehydration of the aqueous acetic acid is effected by azeotropic distillation in conventional manner, the azeotropic distillate being removed through line 60, condensed in condenser 61 and allowed to phase separate in separator 62, the azeotropic agent phase being withdrawn via line 63 and returned as reflux to dehydration zone 55 and the water phase being removed, as mentioned via line 59. Make-up azeotropic agent can be added to line 63 as indicated at 63a.

The acetic acid in line 58, is partly recycled via line 40 and some or all of the balance used to form methyl acetate with methanol to provide the feed for the carbonylation in zone 10. This esterification is carried out in any convenient manner by means well known to persons skilled in the art. Typically, the acetic acid from line 58 is supplied to line 64 which feeds it to esterification zone 70 in which it is reacted with methanol which is supplied through line 72. Acetic acid moieties for reaction with the methanol can also suitably be provided by acetic anhydride supplied through line 30, as mentioned earlier. A suitable acid-reacting catalyst is provided to promote the esterification reaction. The esterification reaction mixture which comprises methyl acetate, water, acetic acid and methanol, is then separated using conventional distillation techniques. Such distillation involves multiple distillations, indicated diagrammatically in the drawing by a distillation zone 80. From zone 80 methyl acetate is withdrawn through line 82 which communicates with line 74 to provide feed for the carbonylation reaction taking place in zone 10. At the same time, acetic acid is withdrawn through line 84 which communicates with line 64 which returns the acetic acid to the esterification reaction in zone 70, and unreacted methanol and some of the methyl acetate is similarly withdrawn via line 86 and recycled to esterification zone 70. By-product water is removed from the system through line 88. Additional methyl acetate, if desired, is supplied to line 14 via line 90. Excess acetic acid in line 58 is withdran via line 91.

As previously mentioned, the carbonylation reaction involving methyl acetate and carbon monoxide which is carried out in carbonylation zone 10 is facilitated by a catalyst, most suitably a Group VIII metal, for example, a Group VIII noble metal, i.e., rhodium, iridium, ruthenium, palladium, osmium and platinum, as disclosed in Belgian Pat. Nos. 819,455 and 839,322, or a nickel catalyst as described in U.S. Pat. Nos. 4,002,677 and 4,002,678. The disclosures of these two U.S. patents are incorporated herein by reference. Thus, in the case of a Group VIII noble metal catalyst, the Group VIII noble metal can be employed in any convenient form, viz. in the zero valent state or in any higher valent form. For example, the catalyst may be the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Complexes of the metals can be employed, e.g. the metal carbonyls, such as iridium and rhodium carbonyls, e.g. hexarhodium hexadecacarbonyl, or as other complexes such as the carbonyl halides, e.g. iridium tri-carbonyl chloride $[Ir(CO)_3Cl]_2$ or chlorodicarbonyl rhodium dimer, or the acetylacetonates, e.g. rhodium acetylacetonate $Rh(C_5H_7O_2)_3$. It will be understood that the foregoing compounds and complexes and classes of compounds and complexes are merely illustrative of suitable forms of the Group VIII noble metal catalyst and are not intended to be limiting.

The metal employed may contain impurities normally associated with the commercially available metal or metal compounds, and need not be purified any further. Thus, the commercially available metal or metal compound is suitably employed.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 100,000 mols of ester, preferably 1 mol per 100 to 10,000 mols of ester, and most preferably 1 mol per 500 to 2,000 mols of ester.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like the other reactants, should, however, be essentially dry, i.e., the CO and the other reactants should be reasonably free from water. The presence of minor amounts of water such as may be found in the commercial forms of the reactants is, however, acceptable. Hydrogen, which may be present in very small (trace) amounts as an impurity, is not objectionable and even may tend to stabilize the catalyst.

It has been previously found that the cavity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of Groups IA, IIA and IIIA as are metals of Group VIB and the non-noble metals of Group VIII. In general, the most suitable elements are lithium, magnesium, calcium, titanium, chromium, iron, nickel and aluminum. Most preferred are lithium, aluminum and calcium, especially lithium. The promoters may be used in their elemental form, e.g. as finely-divided or powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts of organic mono-carboxylic acids, e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts, e.g. salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g. as a finely-divided metal, a slight induction period is observed.

The quantity of promoter can vary widely but preferably it is used in the amount of 0.0001 mol to 100 mols per mol of Group VIII noble metal catalyst, most preferably 0.001 to 10 mols per mol of catalyst.

In the working up of the reaction mixtures, e.g. by distillation, as discussed above, the promoter generally remains with the Group VIII metal catalyst, i.e. as one of the least volatile components, and is suitably recycled or otherwise handled along with the catalyst.

The activity of the Group VIII noble metal catalysts described above is also significantly improved, particularly with respect to reaction rate and product concentration, catalyst stability and corrosion inhibition, by the concurrent use of a promoter combination or co-promoter system containing a metal component which is a metal of Groups IVB, VB and VIB, and the non-noble metals of Group VIII, in any of the forms described above, in association or combination with an organo-nitrogen compound or an organo-phosphorus compound wherein the nitrogen and the phosphorus are trivalent.

The organic co-promoter can, in its broader sense, be any organo-nitrogen or organo-phosphorus compound wherein the nitrogen and phosphorus are trivalent. Preferably, however, the organo-nitrogen co-promoter is an amine, especially a tertiary amine of the

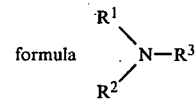

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine tetraacetic acid, and the like, or a heterocyclic amine such as pyridine, picoline, quinoline, methylquinoline, hydroxy quinoline, pyrrole, pyrrolidine, pyrrolidone, and the like, or an imidazole, such as imidazole, methyl imidazole and the like, or an imide of a carboxylic acid which may be monobasic or polybasic and which may be aliphatic or aromatic and preferably contains up to 20 carbon atoms, such as acetic acid, succinic acid, phthalic acid, pyromellitic acid, e.g. N,N-dimethylacetamide, succinimide, phthalimide and pyromellitic diimide, or a nitrile or amide which may be aliphatic or aromatic and preferably contain up to 20 carbon atoms, e.g. acetonitrile, hexamethyl phosphoric triamide, and like imides, nitriles, and amides, or an oxime such as cyclohexanone oxime, and the like. It will be understood, however, that higher molecular weight promoters, e.g. polymeric forms of the organo-nitrogen compounds, may be used such as polyvinylpyridine, polyvinyl pyrrolidone, and the like.

The organo-phosphorus co-promoter is preferably a phosphine of the

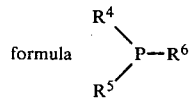

wherein $R^4$, $R^5$ and $R^6$ may be the same or different and are alkyl, cycloalkyl, aryl groups, amide groups or halogen atoms, preferably containing up to 1 to 20 carbon atoms in the case of alkyl and cycloaklyl groups and 6 to 18 carbon atoms in the case of aryl groups. Typical phosphines include trimethylphosphine, tripropylphosphine, tricyohexylphosphine and triphenylphosphine.

Although it is preferred that the organic promoters be added separately to the catalyst system, it is possible to add them as complexes with the Group VIII noble metal such as the trichloro trispyridine rhodium, tris(triphenyl phosphine) rhodium, chlorotris(triphenyl phosphine) rhodium, and chlorocarbonyl bis(triphenyl phosphine) rhodium previously mentioned. Both free organic promoters and complexed promoters can also be used. Indeed, when a complex of the organic promoter and the Group VIII noble metal is used, it is desirable to add free organic promoter as well.

In accordance with a preferred embodiment of the invention, the carbonylation step is carried out in a single reaction zone to which a halide source, e.g. a hydrocarbyl halide such as methyl iodide, and the methyl acetate are both charged and are heated together, preferably in the liquid phase, in the presence of carbon monoxide and in the presence of the Group VIII metal catalyst. It will be understood that the hydrocarbyl halide may be formed in situ and the halide may thus be supplied to the system not only as the hydrocarbyl halide but the halogen moiety may also be supplied as another organic halide or as the hydro-halide or other inorganic halide, e.g. salts, such as the alkali metal or other metal salts, or even as elemental iodine or bromine.

As previously mentioned, in carrying out the carbonylation steps of the invention, a wide range of temperatures, e.g. 20° to 500° C. are suitable but temperatures of 100° to 300° C. are preferably employed and the more preferred temperatures generally lie in the range of 125° to 250° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but excessively high pressures, which require special high-pressure equipment, are not necessary. In general, the reaction is effectively carried out by employing a carbon monoxide partial pressure which is preferably 5 to 2,000 psi, although carbon monoxide partial pressures of 0.1 to 15,000 psi can also be employed. The total pressure is that required to provide the desired CO partial pressure and preferably that required to maintain the liquid phase. Typically, total pressures up to about 3,000 psig are used but most preferably they are at most about 1,000 psig. The reaction can be advantageously carried out in an autoclave or similar apparatus.

The ratio of ester to the halide in the reaction system can vary over a wide range. Typically, there are used 1 to 500 equivalents of the ester per equivalent of halide, preferably 1 to 200 equivalents per equivalent. Thus, there are typically used 1 to 500 mols, preferably 1 to 200 mols of ester per mol of halide reactant. By maintaining the partial pressure of carbon monoxide at the values specified, adequate amounts of the reactant are always present to react with the hydrocarbyl halide.

The effluent from the carbonylation step is treated, e.g. distilled, by conventional techniques to separate the product acetic anhydride from it and to recover streams containing unreacted methyl acetate, iodine moieties, catalyst components (and promoter components, if employed), all of which are recycled to the carbonylation reaction for reuse. As indicated above, the distillation of the carbonylation effluent is conveniently effected in one or more distillation units, e.g. flash and/or fractional distillation devices, represented in the drawing by distillation zone 20. In distillation zone 20 temperatures of 50° to 180° C. and pressures of 0 to 60 psig typically prevail.

The reaction of the acetic anhydride with the cellulose and the recovery of the product cellulose acetate and the co-produced acetic acid, including the dehydration of the dilute acetic acid streams to produce concentrated glacial acetic acid, are, as previously mentioned, readily carried out in known manner in accordance with conventional techniques with which a person skilled in the art is fully familiar, as described. With respect to the acetylation of cellulose, in addition to the description above, additional examples of suitable processes can be found, for instance, in Stone U.S. Pat. No. 2,136,030, Malm et al. U.S. Pat. No. 2,353,255, Hincke U.S. Pat. No. 2,521,916, Blume et al. U.S. Pat. No. 2,632,007, Stoneman U.S. Pat. No. 2,635,097 and Touey et al. U.S. Pat. No. 2,861,069. While the foregoing patents refer primarily to batch operations, continuous processes for acetylating cellulose are well-known to persons skilled in the art and in this connection, reference is made to Clevy et al. U.S. Pat. No. 2,801,237.

With regard to recovery of concentrated or glacial acetic acid from the dilute acetic acid streams which are obtained as a result of the acetylation reaction and the treatment of the acetylated product, i.e., the cellulose acetate, azeotropic distillation is the method of choice. The dehydration of acetic acid by azeotropic distillation is a well-known process and various effective azeotropic agents can be used, such as benzene, ketones, e.g., ethyl propyl ketone and dipropyl ketone, and ethers such as ethyl amyl ether and dibutyl ether, esters such as n-propyl acetate and i-propyl acetate, and the like. Typical processes of this type are disclosed in Othmer U.S. Pat. Nos. 2,028,800, 2,076,184, 2,170,834 and 2,184,563. Of course, it is also possible to effect the dehydration by other means such as extractive distillation as disclosed in Hartley U.S. Pat. No. 2,651,604 wherein a dimethoxy polyglycol, e.g. dimethoxy diethylene glycol, is used as the extractive distillation agent.

The acetic acid formed in the above-described operations is employed to produce methyl acetate to be supplied to the carbonylation zone to form additional quantities of acetic anhydride and to complete the cycle of the process of this invention. For this purpose the acetic acid is passed to an esterification zone where it is brought into contact with methanol in the presence of an esterification catalyst. The esterification of acetic acid with methanol is a well-known reaction which is catalyzed by various known catalysts which are acidic in nature, such as sulfuric acid, i.e., Fisher esterification. Preferably, however, a solid catalyst such as an acid-reacting ion exchange resin of known type is advantageously employed, the solid catalyst forming a bed in the esterification zone through which acetic acid and methanol are passed. Esterification catalysts of this type are well known and representative catalysts are described, for example, in U.S. Pat. No. 2,980,731 and U.S.

Pat. No. 3,278,585. Typically, esterification temperatures of 50° to 160° C. are employed, and preferably the esterification is effected at super-atmospheric pressures, e.g., 30 to 200 psig, although lower or higher pressures can be employed, if desired. For best results residence times of the order of 5 to 50 minutes are observed. The esterification reaction theoretically consumes equal molar parts of acetic acid and methanol but an excess of one of the reactants is desirably present, e.g., 50 to 400% excess based upon the other reactant. Preferably, however, the acetic acid is in excess. Providing this excess is readily accomplished merely by recycling it through the system, i.e., recovering it from the esterification effluent and returning it to the esterification feed inlet.

The esterification effluent will comprise product methyl acetate, co-product water, unreacted acetic acid and methanol. This mixture is readily separated in conventional manner by a series of fractional distillations. Typically the mixture is first distilled at a temperature of 40° C. to 130° C. and at a pressure of 10 to 20 psia to separate as a distillate a methanol methyl acetate azeotrope from the remaining methyl acetate and the acetic acid and water. In a subsequent distillation the balance of the methyl acetate is taken overhead by distilling the bottoms from the first distillation at a temperature of 40° C. to 150° C. and at a pressure of 0 to 15 psig. The methanol-methyl acetate azeotrope is returned to the esterification step for reaction with acetic acid and the freed methyl acetate is, in accordance with the invention, supplied as feed to the carbonylation reaction previously described, suitably after dehydration to remove accompanying water. Dehydration can be effected in any conventional manner, e.g., by solvent extraction, for example as described in Curtis U.S. Pat. No. 3,904,676. The wet acetic acid recovered as bottoms from the second distillation is then typically distilled at temperatures in the range of 40° to 160° C. and at atmospheric pressure to dehydrate the acetic acid. The thus recovered acetic acid is then recycled to the esterification zone for conversion to methyl acetate.

As previously mentioned, it is a feature of the integrated cyclic process of this invention that it is possible to carry it out with feeds consisting essentially only of methanol, carbon monoxide and cellulose. The acetic acid concurrently produced with the cellulose acetate may be partly withdrawn for other purposes, and may be insufficient to provide all of the methyl acetate needed for the carbonylation reaction. Additional methyl acetate is, accordingly, produced in the esterification zone from some of the acetic anhydride produced in the carbonylation zone in accordance with the equation

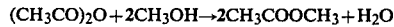

Of course, acetic acid and/or methyl acetate can be supplied from an external source if it is desired to remove all of the acetic anhydride not used for cellulose acetate formation from the system. It is preferred, however, to utilize some of this acetic anhydride to produce methyl acetate as described above or by converting it to acetic acid in accordance with the equation

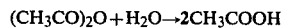

and supplementing the acetic acid in line 64 with the thus-produced acetic acid.

The following examples will serve to provide a fuller understanding of the invention, but it is to be understood that these examples are given for illustrative purposes only and are not to be interpreted as being limitative of the invention. In the examples, all parts are on a molar basis, unless otherwise indicated.

EXAMPLE I

Using an apparatus system such as illustrated in the drawing, a carbonylation zone 10 in the form of a stirred pressure reactor is filled to the level of withdrawal line 19 with a mixture composed of approximately 93.5 mol percent methyl acetate, 2.25 mol percent methyl iodide, 4 mol percent lithium iodide and 0.25 mol percent rhodium acetate. This mixture is heated to about 170° C. and carbon monoxide is introduced into the reactor to provide and maintain a partial pressure of carbon monoxide of 300 psi, resulting in a total pressure of about 500 psig. Continuous liquid feed to the reactor is then begun and liquid reaction product is withdrawn and distilled to separate a product acetic anhydride stream and to provide recycle streams containing some acetic anhydride as well as unreacted methyl acetate and iodine, lithium and rhodium values resulting from the methyl iodide, lithium iodide and rhodium acetate initially charged, the recycle streams being continuously returned to the reactor. The reaction is carried out to provide a residence time in the reactor of about three hours. Thus, there are continuously fed approximately 750 parts per hour of methyl acetate (including 490 parts recycle methyl acetate) along with recycle of the iodine, lithium and rhodium values representing 18 parts per hour of methyl iodide, 32 parts per hour of lithium iodide and 2 parts per hour of rhodium acetate, together with recycle acetic anhydride, the recycle streams being obtained as described below. The reaction mixture is continuously withdrawn at the rate of 1,000 parts per hour and passed into distillation zone 20. In distillation zone 20, the reactor effluent is first flashed at about 50 psia and 150° C. The heavy liquid from the flash, which contains the catalyst components, some methyl acetate and some acetic anhydride is recycled to carbonylation zone 10 at the rate of approximately 300 parts per hour. The vapor from the flash is fractionally distilled at a pressure of about 50 psia and at a temperature in the range of 50° to 160° C. to separate approximately 440 parts per hour of a "lights" fraction comprising methyl acetate and methyl iodide, which is recycled to carbonylation zone 10 via line 26. The bottoms from this distillation are comprised of approximately 260 parts per hour of product acetic anhydride which are fed via line 28 to acetylation zone 35 for reaction with cellulose in the presence of recycle acetic acid from line 40. Acetylation is carried out continuously as described in Clevy et al. U.S. Pat. No. 2,801,237, following the procedure described in the example, using cellulose, suitably in the form of cotton linters, impregnated with twice its weight of the recycle acetic acid. The feed of acetic anhydride is, as mentioned, approximately 260 parts per hour and the cellulose and the other components of the reaction system are supplied in amounts to provide the relative proportions set forth in the patent. Following the dilution of the reaction mixture with the mixture of 60% acetic acid and 40% water, the cellulose acetate is hydrolyzed and precipitated in conventional manner and then purified. Hydrolysis and precipitation are carried out in the usual way such as described on pages 339 and 340 of Volume 3 of the "Encyclopedia of Polymer Science and Technology" published by Interscience Publishers (1965). These steps are carried out batch-wise but by using a plurality of vessels in parallel and switching from one to the other, the continuous supply from the acetylation reactor and the continuous supply of dilute acetic acid to the dehydration step are readily accommodated.

The dilute acetic acid obtained from the hydrolysis and precipitation, combined with the dilute acetic acid obtained from washing the cellulose acetate, is then continuously dehydrated by azeotropic distillation with normal propyl acetate as described in Othmer U.S. Pat. No. 2,028,800. The dehydrated acetic acid thus produced is divided to provide a recycle stream which is returned via line 40 to supply acetic acid for impregnating the cellulose and for incorporation in the acetylation reaction mixture, as well as for hydolysis and precipitation of the cellulose acetate. Additional so-recovered acetic acid provides approximately 260 parts per hour of acetic acid which is fed to line 64 and supplied to esterification zone 70.

Along with the acetic acid from line 64, esterification zone 70 which is suitably defined by a tank which contains a bed of an acidic ion-exchange results (Dowex 50W) and is operated at about 70° C. and 120 psia, is fed with 260 part per hour of methanol, and a recycle stream of 50 parts per hour of a methanol-methyl acetate azeotropic mixture is supplied via line 86. The reaction effluent from esterification zone 70 enters distillation zone 80 in which there is distilled as overhead the above-mentioned methanol-methyl acetate azeotrope which is recycled to the esterification reaction via line 86 at the rate of 50 parts per hour. Then about 260 parts per hour of methyl acetate product (accompanied by a small amount of water) are taken overhead in a further distillation which is carried out at atmospheric pressure and at temperatures in the range of 50° to 130° C. The bottoms from this distillation comprising water and acetic acid are then separated by distillation at a pressure of about 30 psia and at temperatures in the range of 120° to 150° C. As a result of this distillation, the separated water is drained via line 88 and about 500 parts per hour of acetic acid are recycled to esterification zone 70 via line 84. The methyl acetate is substantially dehydrated and then fed to carbonylation zone 10 via line 82.

Ordinarily, there will be sufficient acetic acid for esterification to supply the quantity of methyl acetate required for carbonylation. If, however, acetic acid is required for other purposes, the acetic acid available for esterification to methyl acetate may be less than that needed. This, short-fall of acetic acid can, of course, be compensated for by supplying make-up acetic acid or methyl acetate as required. It is a feature of the invention, however, that the process can effectively be carried out using only carbon monoxide, cellulose and methanol as feed materials. The following example illustrates how any short-fall in acetic acid availability can be readily met without requiring make-up methyl acetate or acetic acid from an external source.

EXAMPLE II

Using the apparatus system described in Example I, carbonylation zone 10 is continuously fed as described in Example I but with an additional 40 parts per hour of methyl acetate as fresh feed, and the reaction mixture is maintained at a temperature of about 170° C. and carbon monoxide is continuously introduced to maintain a partial pressure of carbon monoxide of 300 psi and a total pressure of 500 psig, as described in Example I. The reaction mixture is withdrawn at the rate of approximately 1,040 parts per hour and distilled in distillation zone 20 under the conditions described in Example I. As a result of such distillation there are obtained approximately 300 parts per hour of acetic anhydride, 280 parts per hour of which are supplied to the acetylation zone 35 and the remaining 20 parts per hour are fed via line 39 to esterification zone 70. The acetylation, hydrolysis, precipitation and dehydration are carried out as described in Example I. Notwithstanding the processing and other losses, additional acetic anhydride compensates for the losses and the full 260 parts per hour of acetic acid are available for esterification to methyl acetate. In the esterification step, esterification zone 70 is fed with 300 parts per hour of methanol via line 72. As a result of the esterification of the combined acetic acid and acetic anhydride, there are produced 300 parts per hour of methyl acetate which provide the amount of this raw material necessary to compensate for the losses and to produce the additional acetic anhydride required in the esterification step. In this manner the process can be continued for prolonged periods while being supplied only with methanol, cellulose and carbon monoxide as raw materials.

In the foregoing example, reference has been made to a short-fall of acetic acid with particular reference to processing and other losses but a short-fall may also occur when the cellulose acetate is not hydrolyzed to the conventional degree and cellulose triacetate is recovered as the product, since fewer acetic acid moieties are released. The process is thus applicable both to the production of fully acetylated cellulose as well as partially hydrolyzed cellulose acetate.

Ordinarily, because of the use of excess acetic anhydride in relation to cellulose and the substantial hydrolysis of that excess acetic anhydride, there is in general no short-fall. However, it is also possible to compensate for any short-fall in the conversion of the dehydrated acetic acid to methyl acetate. This is done by producing more acetic anhydride than is required to be fed to the cellulose acetylation step and using this acetic anhydride to supplement the acetic acid in the esterification step as well as to supply by-product acetic anhydride, if desired. This is illustrated in the following example.

EXAMPLE III

Again using the system described in Example I, carbonylation zone 10 is continuously fed with approximately 1,250 parts per hour of methyl acetate, (460 parts fresh fed and 790 parts recycle), and sufficient methyl iodide, lithium iodide and rhodium acetate (32 parts methyl iodide, 56 parts LiI, and 3 parts Rh(OAc)$_3$ is initially supplied to provide the concentrations specified in Example I. The reaction mixture is maintained at a temperature of about 170° C. and carbon monoxide is continuously introduced to maintain a partial pressure of carbon monoxide of 300 psi and a total pressure of 500 psig as described in Example I. The reaction mixture containing acetic anhydride and methyl acetate along with the catalyst and iodine compounds is withdrawn at the rate of approximately 1,770 parts per hour and passed into distillation zone 20. In distillation zone 20, the reactor effluent is first flashed at about 50 psia and 150° C. The heavy liquid from the flash, which contains the catalyst components, some methyl acetate and some acetic anhydride is recycled to carbonylation zone 10 at the rate of approximately 530 parts per hour.

The vapor from the flash is fractionally distilled at a pressure of about 50 psia and at a temperature in the range of 50° to 160° C. to separate approximately 780 parts per hour of a "lights" fraction comprising methyl acetate and methyl iodide, which is recycled to carbonylation zone 10 via line 26. The bottoms from this distillation are composed of approximately 460 parts per hour of product acetic anhydride, 100 parts per hour of this product are withdrawn via line 32 and 100 parts per hour supplied to esterification zone 70 via line 30. The remainder of the acetic anhydride (260 parts per hour) are fed via line 28 to cellulose acetate formation zone 35 as in Example I and the acetylation, hydrolysis, precipitation and dehydration are carried out as described in Example I, 260 parts per hour of acetic acid being available to supply to the esterification zone via line 64. Along with the acetic acid from line 64 and the acetic anhydride from line 30, esterification zone 70 (70° C. and 120 psia) is fed with 460 parts per hour of methanol, and a recycle stream of 90 parts per hour of a methanol-methyl acetate azeotropic mixture is supplied via line 86. The reaction effluent from esterification zone 70 enters distillation zone 80 in which there is distilled as overhead the above-mentioned methanol-methyl acetate azeotrope which is recycled to the esterification reaction via line 86 at the rate of 90 parts per hour. Then about 460 parts per hour of methyl acetate product (accompanied by a small amount of water) are taken overhead in a further distillation which is carried out at atmospheric pressure and at temperatures in the range of 50° C. to 130° C. The bottoms from this distillation comprising water and acetic acid are then separated by distillation at a pressure of about 30 psia and at temperatures in the range of 120° to 150° C. As a result of this distillation, the separated water is drained via line 88 and about 900 parts per hour of acetic acid are recycled to esterification zone 70 via line 84. The methyl acetate is substantially dehydrated and then fed to carbonylation zone 10.

If there is a short-fall of acetic acid required for the desired production of methyl acetate in the esterification reaction, this short-fall can be readily eliminated by using some of the acetic anhydride recovered via line 32. Again, it it seen that the process of this invention can be continued for prolonged periods of time while being supplied only with methanol, carbon monoxide and cellulose as raw materials.

What is claimed is:

1. A cyclic integrated process for the preparation of cellulose acetate from methanol, cellulose and carbon monoxide which comprises the steps of:
   (1) carbonylating methyl acetate to produce acetic anhydride in a carbonylation zone;
   (2) reacting at least some of the so-produced acetic anhydride with cellulose to convert at least part of said acetic anhydride to cellulose acetate and acetic acid;
   (3) dehydrating said acetic acid by removing at least a portion of the water therefrom;
   (4) esterifying said dehydrated acetic acid with methanol in an esterification zone to form methyl acetate for step (1); and
   (5) introducing methyl acetate produced in step (4) into said carbonylation zone.

2. A process as defined in claim 1, wherein at least a portion of said acetic anhydride produced in said carbonylation zone is introduced into said esterification zone for reaction with said methanol to produced methyl acetate.

3. A process as defined in claim 1, wherein step (1) is carried out in the presence of a catalyst comprising a Group VIII metal.

4. A process as defined in claim 3, wherein the catalyst comprises a Group VIII noble metal.

5. A process as defined in claim 3, wherein the catalyst comprises nickel.

* * * * *